US008690857B2

(12) United States Patent
Yeung et al.

(10) Patent No.: US 8,690,857 B2
(45) Date of Patent: Apr. 8, 2014

(54) ALLEVIATE BACK PAIN WITH LACTIC ACID INHIBITORS

(75) Inventors: Jeffrey Eric Yeung, San Jose, CA (US); Teresa Tan Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 183 days.

(21) Appl. No.: 13/136,129

(22) Filed: Jul. 25, 2011

(65) Prior Publication Data

US 2012/0022425 A1 Jan. 26, 2012

Related U.S. Application Data

(60) Provisional application No. 61/400,223, filed on Jul. 23, 2010.

(51) Int. Cl.
*A61M 31/00* (2006.01)

(52) U.S. Cl.
USPC .......................................................... 604/506

(58) Field of Classification Search
USPC ....... 606/79, 86 A, 248, 279, 297; 604/8, 506
See application file for complete search history.

(56) References Cited

U.S. PATENT DOCUMENTS

| | | | | |
|---|---|---|---|---|
| 3,094,122 | A * | 6/1963 | Gauthier et al. | 604/164.01 |
| 7,879,097 | B2 * | 2/2011 | Lambrecht et al. | 623/17.11 |
| 7,938,818 | B2 * | 5/2011 | Yeung | 604/506 |
| 8,092,541 | B2 * | 1/2012 | Peckham | 623/17.16 |
| 8,226,600 | B2 * | 7/2012 | Yeung et al. | 604/93.01 |
| 2003/0158604 | A1 * | 8/2003 | Cauthen et al. | 623/17.16 |
| 2006/0206116 | A1 * | 9/2006 | Yeung | 606/80 |
| 2008/0103504 | A1 * | 5/2008 | Schmitz et al. | 606/79 |
| 2008/0200972 | A1 * | 8/2008 | Rittman et al. | 607/117 |
| 2008/0312636 | A1 * | 12/2008 | Miller et al. | 604/508 |
| 2009/0082719 | A1 * | 3/2009 | Yeung | 604/28 |
| 2009/0204119 | A1 * | 8/2009 | Bleich et al. | 606/79 |
| 2009/0254061 | A1 * | 10/2009 | Baron | 604/506 |
| 2010/0030105 | A1 * | 2/2010 | Noishiki et al. | 600/567 |
| 2010/0030241 | A1 * | 2/2010 | Yeung et al. | 606/146 |
| 2011/0022143 | A1 * | 1/2011 | North | 607/117 |

OTHER PUBLICATIONS

Deyo R A, Weinstein J N: Low back pain, N Eng J Med, 344(5) February, 363-370, 2001.*
Boswell M V, et. al.: Interventional Techniques: Evidence-based practice guidelines in the management of chronic spinal pain, Pain Physician, 10:7-111, ISSN 1533-3159, 2007.*
Manchikanti L, Derby R, Benyamin R M, Helm S, Hirsch J A: A systematic review of mechanical lumbar disc decompression with nucleoplasty, Pain Physician; 12:561-572 ISSN 1533-3159, 2009.*

(Continued)

*Primary Examiner* — Nicholas Lucchesi
*Assistant Examiner* — Diva K Chander
(74) *Attorney, Agent, or Firm* — Carol Titus; GSS Law Group

(57) ABSTRACT

The intervertebral disc is avascular. Nutrients and waste are diffused through adjacent vertebral bodies into the disc. As we age, calcified layers form between the disc and vertebral bodies, blocking diffusion of nutrients, oxygen and pH buffer in blood. Under anaerobic conditions, lactic acid is produced, irritating nerve endings and causing nonspecific pain. In addition, the disc begins to starve and flatten. The weight shifts abnormally from disc to the facet joints causing strain and back pain.

Lactic acid inhibitor inhibits production of lactic acid from pyruvate within the disc to reduce or alleviate back pain.

20 Claims, 8 Drawing Sheets

(56) References Cited

OTHER PUBLICATIONS

Stairmand J W, Holm S, Urban J P G: Factor influencing oxygen concentration gradients in disc, Spine, vol. 16, 4, 444-449, 1991.*

Maroudas A, Stockwell R A, Nachemson A, Urban J: Factors involved in the nutrition of the human lumbar intervertebral disc: Cellularity and diffusion of glucose in vitro, J. Anat., 120, 113-130, 1975.*

Urban J P, Smith S, Fairbank J C T: Nutrition of the Intervertebral Disc, Spine, 29 (23), 2700-2709, 2004.*

Benneker L M, Heini P F, Alini M, Anderson S E, Ito K: Vertebral endplate marrow contact channel occlusions & intervertebral disc degeneration, Spine V30, 167-173, 2005.*

Holm S, Maroudas A, Urban J P, Selstam G, Nachemson A: Nutrition of the intervertebral disc: solute transport and metabolism, Connect Tissue Res., 8(2): 101-119, 1981.*

Diamant B, Karlsson J, Nachemson A: Correlation between lactate levels and pH of patients with lumbar rizopathies, Experientia, 24, 1195-6, 1968.*

Nachemson A: Intradiscal measurements of pH in patients with lumbar rhizopathies. Acta Orthop Scand, 40, 23-43, 1969.*

Keshari K R, Lotz J C, Link T M, Hu S, Majumdar S, Kurhanewicz J: Lactic acid and proteoglycans as metabolic markers for discogenic back pain, Spine, vol. 33(3):312-317, 2008.*

Diamant B, Karlsson J, Nachemson A: Correlation between lactate levels and pH of patients with lumbar rizopathies. Experientia, 24, 1195-1196, 1968.*

Reference: Kitano T, Zerwekh J, Usui Y, Edwards M, Flicker P, Mooney V: Biochemical changes associated with the symptomatic human intervertebral disk, Clinical Orthopaedics and Related Research, 293, 372-377, 1993.*

Scott J E, Bosworth T R, Cribb A M, Taylor J R: The chemical morphology of age-related changes in human intervertebral disc glycosaminoglycans from cervical, thoracic and lumbar nucleus pulposus and annulus fibrosus. J. Anat., 184, 73-82, 1994.*

Diamant B, Karlsson J, Nachemson A: Correlation between lactate levels and pH of patients with lumbar rizopathies, Experientia, 24, 1195-1196, 1968.*

Nachemson A: Intradiscal measurements of pH in patients with lumbar rhizopathies, Acta Orthop Scand, 40, 23-43, 1969.*

Dunlop R B, Adams M A, Hutton W C: Disc space narrowing and the lumbar facet joints, Journal of Bone and Joint Surgery—British Volume, vol. 66-B, Issue 5, 706-710, 1984.*

Andersson G B J, Schultz A B: Effects of fluid on mechanical properties of intervertebral discs, J. Biomechanics, vol. 12, 453-458, 1979.*

* cited by examiner

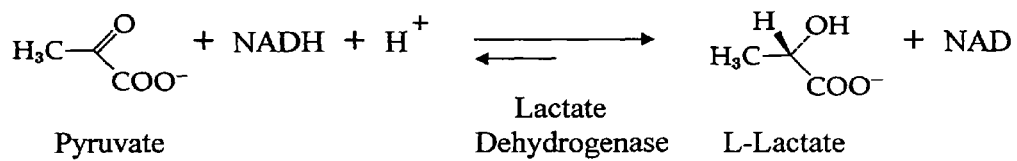
Figure 6
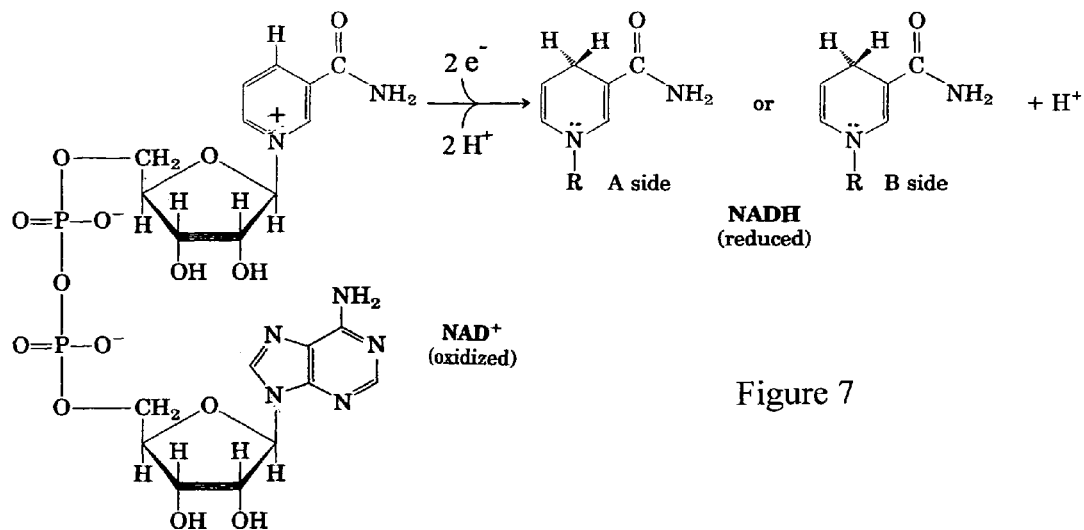
Figure 7
Figure 8
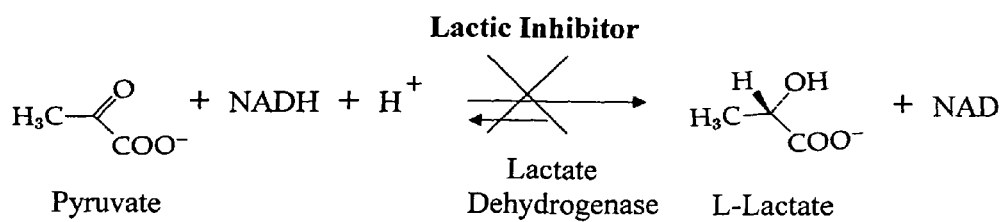

ALLEVIATE BACK PAIN WITH LACTIC ACID INHIBITORS

CROSS-REFERENCE

This application claims priority of U.S. Provisional Application 61/400,223, entitled Alleviate Back Pain with Lactic Acid Inhibitor, filed on Jul. 23, 2010 by Jeffrey E. Yeung and Teresa T. Yeung.

FIELD OF INVENTION

Diffusion of nutrients, oxygen and pH buffer into avascular intervertebral discs is limited to the depths of diffusion zones near superior and inferior endplates. Lactic acid produced anaerobically in the mid layers of the nucleus leaks from the disc to cause acid burn and persistent back pain. This invention relates to chemicals, device and method for inhibiting production of lactic acid within the avascular disc. As a result, back pain from lactic acid burn is reduced or alleviated.

BACKGROUND

Chronic back pain is an epidemic. Nerve impingement is not seen by CT or MRI in about 85% of back pain patients [Deyo R A, Weinstein J N: Low back pain, N Eng J Med, 344(5) February, 363-370, 2001. Boswell M V, et. al.: Interventional Techniques: Evidence-based practice guidelines in the management of chronic spinal pain, Pain Physician, 10:7-111, ISSN 1533-3159, 2007]. In fact, lumbar disc prolapse, protrusion, or extrusion account for less than 5% of all low back problems, but are the most common causes of nerve root pain and surgical interventions (Manchikanti L, Derby R, Benyamin R M, Helm S, Hirsch J A: A systematic review of mechanical lumbar disc decompression with nucleoplasty, Pain Physician; 12:561-572 ISSN 1533-3159, 2009). The cause of chronic back pain in most patients has been puzzling to both physicians and patients.

Studies indicate back pain is correlated with high lactic acid in the disc. Leakage of the acid causes acid burn and persistent back pain. In addition, as the disc degenerates and flattens, the compressive load is shifted from the flattened disc to facet joints, causing pain. Both lactic acid burn and strain of the facet joints are not visible under CT or MRI.

SUMMARY OF INVENTION

Lactic acid is anaerobically produced within avascular intervertebral discs. Acid hydrolysis of disc matrix creates fissures at the annulus. Lactic acid leaks from the nucleus through fissures to burn surrounding nerves and cause persistent back pain.

Lactic acid inhibitor inhibits production of lactic acid from pyruvate within discs to reduce or alleviate back pain.

| REFERENCE NUMBERS | |
|---|---|
| 100 | Intervertebral disc |
| 105 | Endplate |
| 106A | Superior diffusion zone |
| 106B | Inferior diffusion zone |
| 107 | Capillaries (blood vessels) |
| 108 | Calcified layers |
| 114 | Annular delamination |
| 115 | Epiphysis |
| 118 | Nerve |
| 119 | Vascular buds at the endplate |
| 121 | Fissure |
| 122 | Buffer or alkaline chemical |
| 123 | Spinal cord |
| 126 | Disc shunt |
| 128 | Nucleus pulposus |
| 129 | Facet joint |
| 131 | Nutrients, oxygen and pH buffering solute |
| 133 | Transverse process |
| 142 | Superior articular process |
| 143 | Inferior articular process |
| 159 | Vertebral body |
| 162 | Lactic acid |
| 163 | Lactic acid inhibitor |
| 193 | Muscle |
| 194 | Spinal nerve root |
| 195 | Posterior longitudinal ligament |
| 276A | Syringe |
| 276B | Disc injecting needle |
| 278 | Pedicle |
| 378 | Annulus or annular layer |
| 505 | Skin |

DESCRIPTION OF THE DRAWINGS

FIG. 6 shows anaerobic metabolism of pyruvate to lactate by oxidizing nicotinamide adenine dinucleotide (NADH), catalyzed by lactate dehydrogenase (enzyme) in the avascular disc.

FIG. 7 showing the oxidized nicotinamide adenine dinucleotide NAD+ is reduced by 2 electrons and two protons to NADH, capable of metabolizing pyruvate to lactate.

FIG. 8 shows a lactic inhibitor inhibiting the conversion of pyruvate to lactate. The inhibitor can be irreversible, reversible, competitive, non-competitive, un-competitive or mixed inhibitor.

DETAILED DESCRIPTION OF THE EMBODIMENTS

Figure 1:
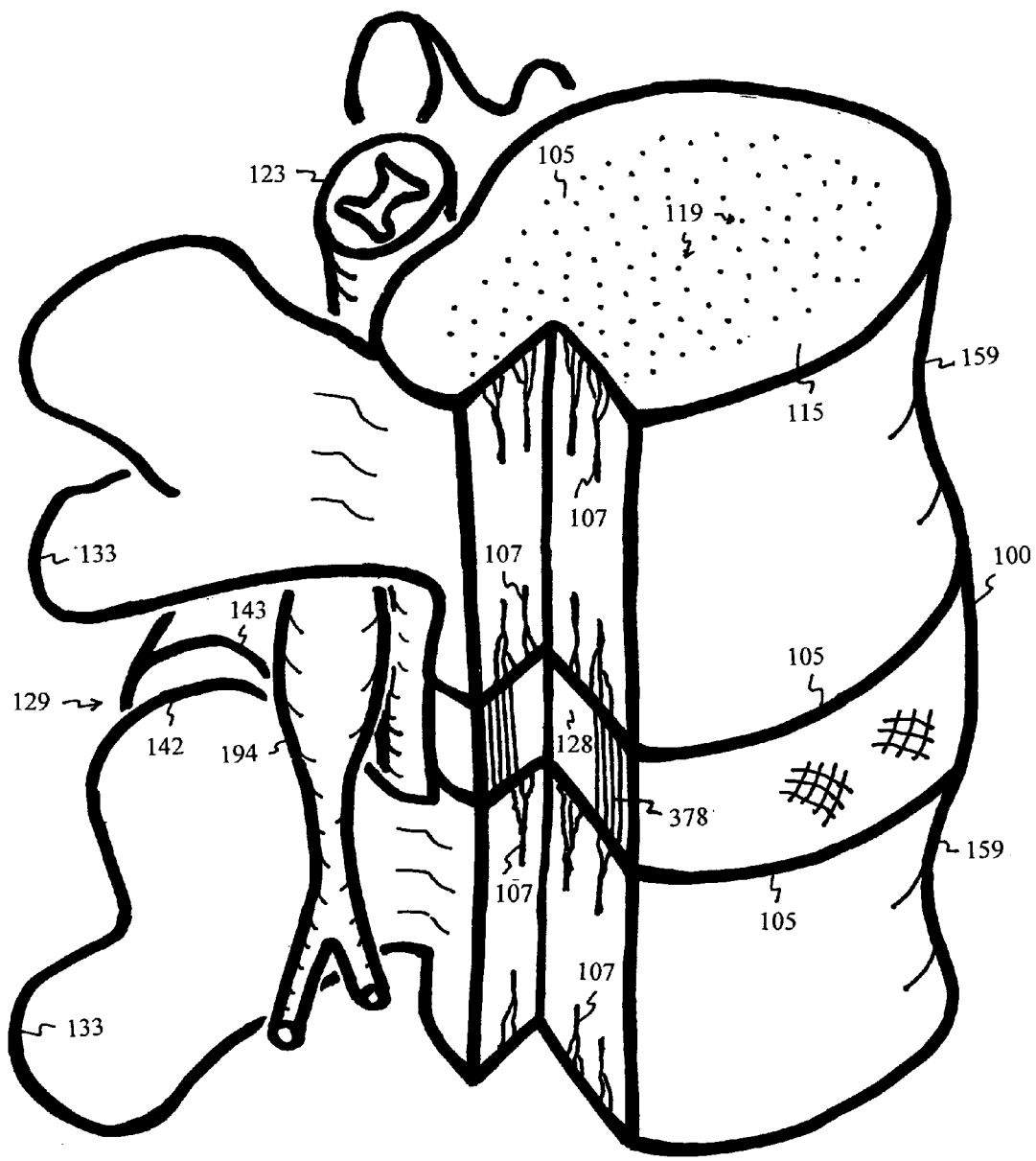
FIG. 1 shows a cut-away spinal segment, showing vascular buds 119 of capillaries 107 embedded in endplates 105 to nourish cells in the avascular disc 100.
Figure 2:
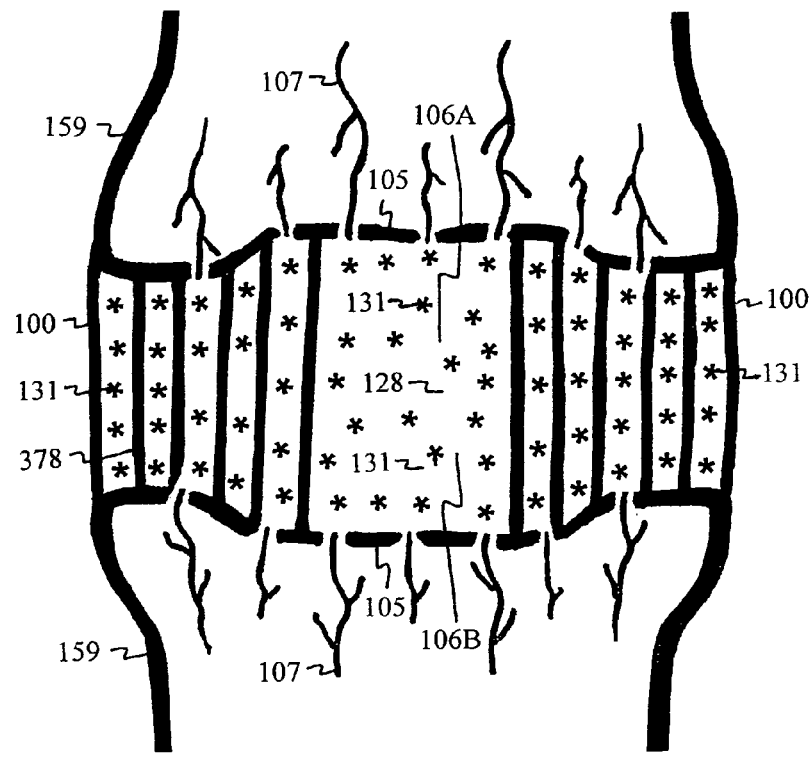
FIG. 2 shows a longitudinal view of a healthy spinal segment with nutrients 131 supplied through vascular buds of capillaries 107 at the endplates 105 to feed the cells within the disc 100.

Intervertebral discs are avascular (no blood vessels). Nutrients, oxygen and pH buffer 131 essential for disc cells are supplied by the capillaries 107 in the vertebral bodies 159 and diffused from both superior and inferior endplates 105 into the disc 100, as shown in FIGS. 1 and 2. Normal blood pH is tightly regulated between 7.35 and 7.45, mainly by the pH buffering bicarbonate dissolved in blood plasma diffused through capillaries 107 and vascular buds 119 into the disc 100.

Figure 3:
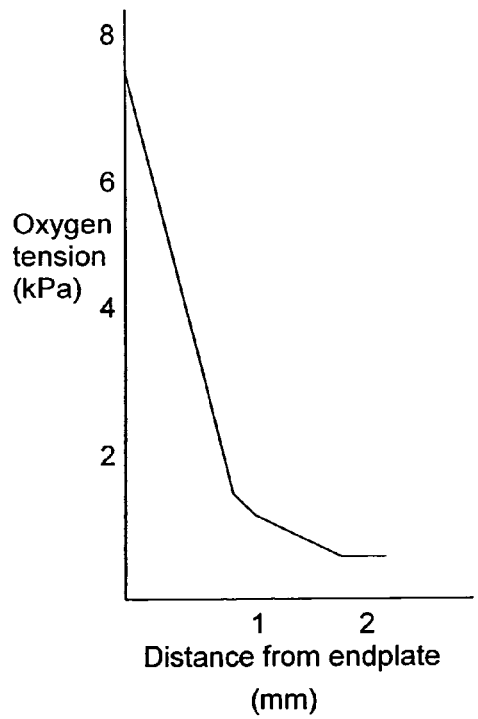
FIG. 3 shows a graph of distance from endplate versus oxygen concentration.

However, depth of diffusion is shallow into thick human discs 100. The calculated depth of oxygen diffusion from the endplates 105 is summarized in FIG. 3 (Stairmand J W, Holm S, Urban J P G: Factor influencing oxygen concentration gradients in disc, Spine, Vol. 16, 4, 444-449, 1991).

Similarly, calculated depths of glucose diffusion are less than 3 mm from superior and inferior endplates (Maroudas A, Stockwell R A, Nachemson A, Urban J: Factors involved in the nutrition of the human lumbar intervertebral disc: Cellularity and diffusion of glucose in vitro, J. Anat., 120, 113-130, 1975). Nearly all animals have thin discs; depths of diffusion of nutrients and oxygen seem to be sufficient. Lumbar discs of a large sheep weighing 91 kg (200 pounds) are less than 4 mm thick. However, human lumbar discs are about 7-12 mm thick. Mid layers of our thick discs 100 are highly vulnerable to severe nutritional and oxygen deficiency.

Figure 4:
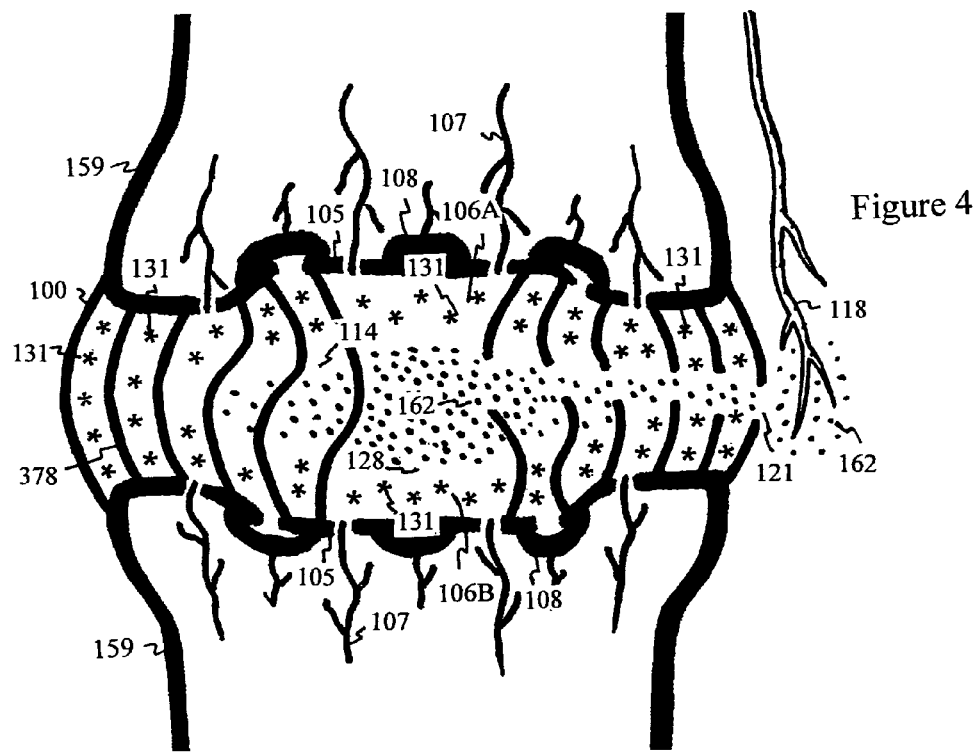
FIG. 4 shows calcified layers 108 accumulated at the endplates 105, partially blocking diffusion of nutrient/oxygen 131 from capillaries 107, leading to anaerobic production of lactic acid 162 to irritate nerves 118.

As we age, calcified layers 108 form and accumulate at the endplates 105, blocking capillaries 107 and further limiting the depth of diffusion of nutrients/oxygen/pH buffer 131 into the disc 100, as shown in FIG. 4. The depth of diffusion of nutrients/oxygen/pH buffer 131 is mainly limited to superior diffusion zone 106A, about zero to 2 mm from the superior endplate 105, and inferior diffusion zone 106B, about zero to 2 mm from the inferior endplate 105. Cell death, matrix degradation and lactic acid 162 accumulation due to starvation and anaerobic conditions are common in the mid layers of the avascular discs 100. Degradation of glycosaminoglycans may provide sugars to fuel the production of lactic acid 162. [Urban J P, Smith S, Fairbank J C T: Nutrition of the Intervertebral Disc, Spine, 29 (23), 2700-2709, 2004. Benneker L M, Heini P F, Alini M, Anderson S E, Ito K: Vertebral endplate marrow contact channel occlusions & intervertebral annulus 378 to keep the annulus bulging outward. As a result, the inner annulus 378 sags inward while the outer annulus 378 bulges outward, creating annular delamination 114 and weakened annular layers 378, possibly initiating fissure 121 formation depicted in FIGS. 4 and 5.

High lactic acid content in discs 100 correlates with back pain. In fact, dense fibrous scars and adhesions, presumably from lactic acid 162 burn, can be found around nerve roots 194 during spinal surgery [Diamant B, Karlsson J, Nachemson A: Correlation between lactate levels and pH of patients with lumbar rizopathies, Experientia, 24, 1195-6, 1968. Nachemson A: Intradiscal measurements of pH in patients with lumbar rhizopathies. Acta Orthop Scand, 40, 23-43, 1969. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008]. Average lactic acid concentration in painful lumbar disc 100 is about 14.5 mM, about 15 cc of fluid per disc (Diamant B, Karlsson J, Nachemson A: Correlation between lactate levels and pH of patients with lumbar rizopathies. Experientia, 24, 1195-1196, 1968).

Figure 5:
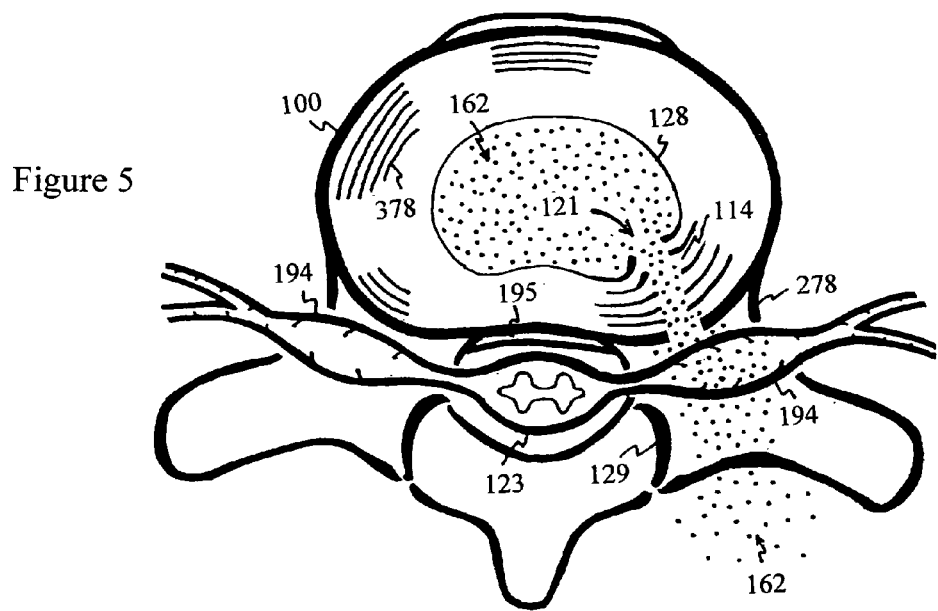
FIG. 5 shows leakage of lactic acid 162 through a fissure 121 burning or irritating the spinal nerve 194.

Under anaerobic condition within the mid layer of the disc 100, lactic acid 162 is produced and leaked from the nucleus 128 through fissures 121 to burn surrounding nerves 118 causing persistent back pain, as depicted in FIGS. 4 and 5. Colored drawings in the U.S. Provisional Application 61/400, 223 entitled Alleviate Back Pain with Lactic Acid Inhibitor, filed on Jul. 23, 2010 by Jeffrey Yeung and Teresa Yeung, show superior and inferior diffusion zones near the calcified endplates and lactic acid zone in the mid layer of the degenerated disc. Similar black and white drawing is depicted in FIG. 4.

Some patients experience leg pain without visible spinal nerve impingement under MRI or CT. Lactic acid 162 can leak from the nucleus 128 through fissures 121 to spinal nerves 194, causing leg pain as depicted in FIG. 5. Leg pain without visible impingement is commonly called chemical radiculitis.

Discography is a common diagnostic technique for identifying or confirming a painful disc 100 before surgical intervention. Intradiscal injection of an X-ray contrast flushes the lactic acid 162 from the nucleus 128 through fissures 121 to adjacent nerves 118, causing instant and excruciating pain. For normal or non-painful discs, discography with mild injection pressure is nearly painless.

Composition Change of the Intervertebral Discs (approximation)

|  | Normal Discs | Painful Discs | % Change from Normal Discs |
|---|---|---|---|
| Glycosaminoglycans | 27.4 ± 2.4% | 14.1 ± 1.1% | −48.5% |
| Collagen | 22.6 ± 1.9% | 34.8 ± 1.4% | +54% |
| Water content | 81.1 ± 0.9% | 74.5 ± 1% | −8.1% |
| Acidity | pH 7.14 $[H^+]: 7.20 \times 10^{-8}$ | pH 6.65-5.70 $[H^+]: 2.23 \times 10^{-7}$ to $2.00 \times 10^{-6}$ | $[H^+]$: +208% to +2,661% | disc degeneration, Spine V30, 167-173, 2005. Holm S, Maroudas A, Urban J P, Selstam G, Nachemson A: Nutrition of the intervertebral disc: solute transport and metabolism, Connect Tissue Res., 8(2): 101-119, 1981].

When glycosaminoglycans diminish, water content and swelling pressure of the nucleus pulposus 128 decrease. The nucleus 128 with reduced swelling pressure can no longer distribute forces evenly against the circumference of the inner (Reference: Kitano T, Zerwekh J, Usui Y, Edwards M, Flicker P, Mooney V: Biochemical changes associated with the symptomatic human intervertebral disk, Clinical Orthopaedics and Related Research, 293, 372-377, 1993. Scott J E, Bosworth T R, Cribb A M, Taylor J R: The chemical morphology of age-related changes in human intervertebral disc glycosaminoglycans from cervical, thoracic and lumbar nucleus pulposus and annulus fibrosus. J. Anat., 184, 73-82, 1994. Diamant B, Karlsson J, Nachemson A: Correlation between lactate levels and pH of patients with lumbar rizopathies, Experientia, 24, 1195-1196, 1968. Nachemson A: Intradiscal measurements of pH in patients with lumbar rhizopathies, Acta Orthop Scand, 40, 23-43, 1969.)

Disc cells can survive without oxygen, but will die without glucose. The central area in the mid layer of the disc 100 is most vulnerable to glucose deficiency and cell death. Holes or vacuoles can be found during dissection of cadaveric discs 100. Nuclei pulpos 128 of degenerated discs 100 are usually desiccated, with reduced swelling pressure and decreased capability to sustain compressive loads. The compressive load is thus transferred to the facet joints 129, pressing the inferior articular processes 143 against the superior articular processes 142 of the facet joints 129, causing strain, wear and/or pain (Dunlop R B, Adams M A, Hutton W C: Disc space narrowing and the lumbar facet joints, Journal of Bone and Joint Surgery—British Volume, Vol 66-B, Issue 5, 706-710, 1984).

A disc 100 with reduced swelling pressure is similar to a flat tire with flexible or flabby side walls. The vertebral body 159 above the soft or flabby disc 100 easily shifts or sways. This is commonly called segmental or spinal instability. The frequent or excessive movement of the vertebral body 159 strains the facet joints 129, which are responsible for limiting the range of segmental mobility. Patients with spinal instability often use their muscles to guard or support their spines to ease facet pain. As a result, muscle tension and aches arise, but are successfully treated with muscle relaxants. Spinal motions, including compression, torsion, extension, flexion and lateral bending, were measured before and after saline injection into cadaveric discs. Intradiscal saline injections reduced all spinal motions in the cadaveric study (Andersson G B J, Schultz A B: Effects of fluid on mechanical properties of intervertebral discs, J. Biomechanics, Vol. 12, 453-458, 1979).

Molecular bonds of collagen and proteoglycans of the disc matrix are vulnerable in acidic conditions, which may lead to matrix decomposition and fissure 121 of the disc 100. Decomposition of the disc matrix leads to disc flattening and spinal instability.

Especially under anaerobic conditions, overall chemical equilibrium between pyruvate and L-lactate 162 strongly favors L-lactate 162 formation with large negative standard free-energy=−25.1 kJ/mol, catalyzed by lactate dehydrogenase and driven by oxidization of NADH to NAD+ as shown in FIG. 6. Through reduction-oxidation reaction, NAD+ is reduced back to NADH by 2 electrons and 2 protons as shown in FIG. 7.

Formation of lactic acid 162 can be inhibited by lactic inhibitors 163. The lactic inhibitor 163 can be irreversible, reversible, competitive, non-competitive, un-competitive or mixed inhibitor 163, as indicated in FIG. 8. The lactic acid inhibitor 163 can be called the lactate dehydrogenase inhibitor 163; lactate dehydrogenase is an enzyme that converts pyruvate to lactic acid. In this patent application, lactic inhibitor 163, lactic acid inhibitor 163 and lactate dehydrogenase inhibitor 163 can be used interchangeably.

The lactic acid inhibitor 163 can be fluoropyruvic acid, fluoropyruvate, levulinic acid, levulinate, oxamic acid, N-substituted oxamic acids, oxamate, oxalic acid, oxalate, beta-bromopropionate, beta-chloropropionate, malonate, sodium formaldehyde bisufite, chloroacetic acid, alpha-chloropropionate, alpha-bromopropionate, beta-iodopropionate, acrylate, acetoin, malic acid, glycolate, diglycolate, acetamide, acetaldehyde, acetylmercaptoacetic acid, alpha ketobutyrate, thioglycolic acid, nicotinic acid, alpha-ketoglutarate, butanedione, hydroxypyruvic, chloropyruvic, bromopyruvic, 2,3-dihydroxy-6-methyl-4-(1-methylethyl)-1-naphthoic acid, diethyl pyrocarbonate, hexyl N,N-diethyloxamate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 (Cibacron Blue 3G-A) urea, methylurea and hydantoic acid, glyoxylate, hydroxybutyrate, 4-hydroxyquinoline-2-3 carboxylic acids, sodium bisulfite, dieldrin, L-(+) beta monofluorolactic acid, fluoro-lactic acid, tartronic acid, mesotartarate, sesquiterpene 8-deoxyhemigossylic acid (2,3-dihydroxy-6-methyl-4-(1-methylethyl)-1-naphthoic acid), or analogues of these chemicals. The lactic acid inhibitor 163 can be dissolved, dispensed or dispersed in aqueous or organic liquid, as a solution or dispersion.

The lactic inhibitor 163 can also be NADH dehydrogenase inhibitor 163. The NADH dehydrogenase inhibitor 163 includes gossypol, polyphenol, dihydroxynaphthoic acids, adenosine diphosphate ribose, rotenone, rotenoid, phenoxan, aureothin, benzimidazole, acetogenin, nitrosothiols, peroxynitrite, carvedilol, arylazido-beta-alanyl NAD+, piericidin A, annonin VI, phenalamid $A_2$, aurachins A and B, thiangazole, fenpyroximate, adriamycin, 4-hydroxy-2-nonenal, pyridine derivatives, 2-heptyl-4-hydroxyquinoline N-oxide, dicumarol, o-phenanthroline or 2,2'-dipyridyl or others, that block conversion of pyruvate to lactic acid 162, causing chronic back pain.

Adenosine triphosphate, ATP, is the high-energy compound essential for driving or energizing biochemical reactions, including the biosynthesis of the water retaining glycosaminoglycans for sustaining compressive loads on the disc 100. Under anaerobic conditions, metabolism of each glucose molecule produces only two ATP and two lactic acids 162, which irritate adjacent nerves 118. By inhibiting conversion of two pyruvates to two lactic acids 162, thirty-six ATP can be produced from each glucose molecule through glycolysis, citric acid cycle and electron transport chain under aerobic conditions to energize disc regeneration and alleviate back pain. Thereby, preservation of pyruvate by inhibiting lactic acid 162 production can reduce back pain and form additional ATP for disc regeneration.

Figure 9:
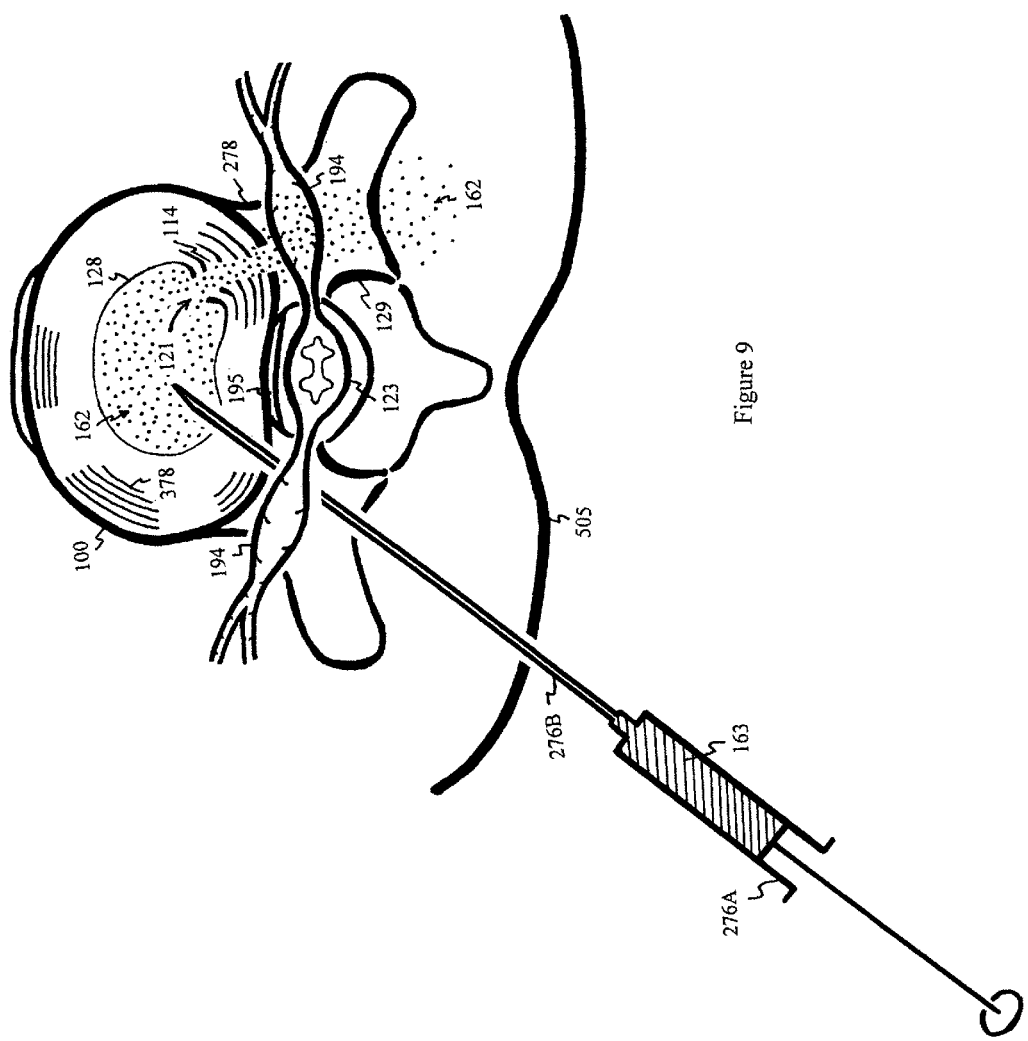
FIG. 9 shows intra-discal injection of lactic acid inhibitor 163 into the painful and degenerated disc 100.

The method of intra-discal injection of lactic inhibitor 163 is similar to the method for discography. Guided by anterior/posterior and lateral views of fluoroscopy, a spinal needle 276B punctures into the painful disc 100. A syringe 276A with a plunger is loaded with lactic inhibitor 163 and connected to the spinal needle 276B for intra-discal injection, as shown in FIG. 9.

The spinal needle 276B has a distal beveled Quincke or Chiba tip to minimize potential damage to nerves during insertion into the patient. L5-S1 lumbar disc 100 is shielded by the iliac. The needle 276B can be elastically curved, capable of resiliently straightened within a straight needle. The straight needle is inserted over the iliac to the outer surface of L5-S1 disc. The curved needle 276B is then deployed from the straight needle, curving into the nucleus 128 of L5-S1 lumbar disc 100 for lactic inhibitor 163 injection. After injection, the curved needle 276B is withdrawn into the straight needle before withdrawing both curved and straight needles from the patient.

Figure 13:
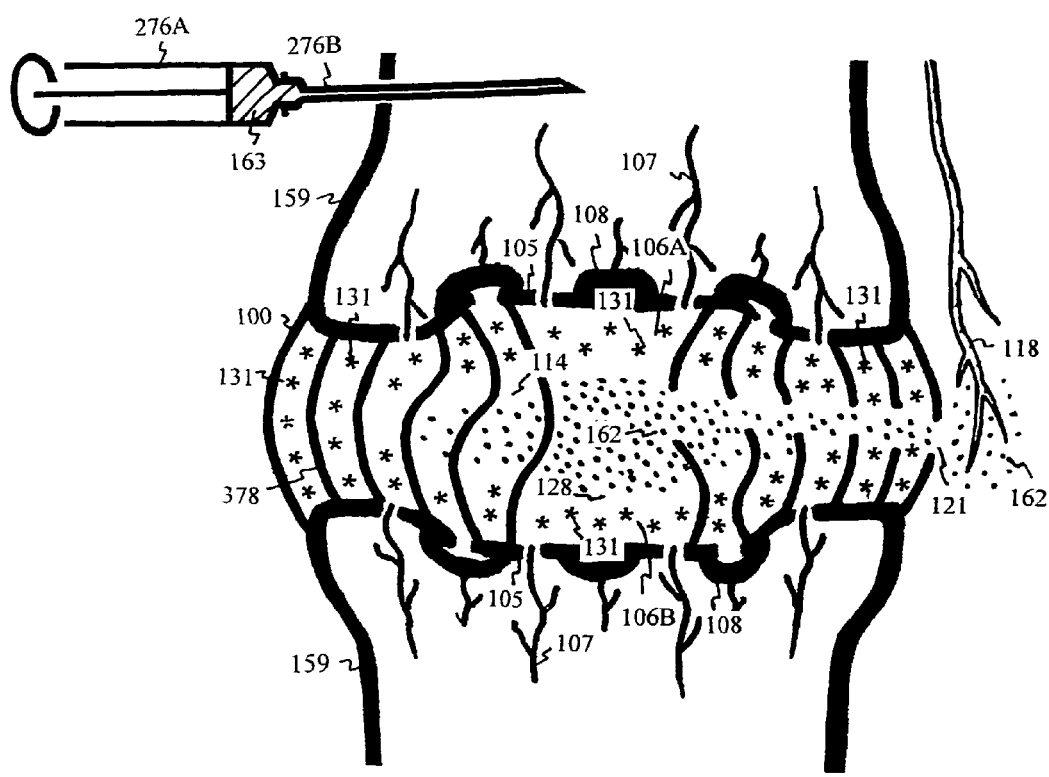
FIG. 13 shows the lactic acid inhibitor 163 can be delivered through intra-vertebral body injection to alleviate back pain.

Generally, nerves are not found within the intervertebral disc 100, but nerves are found at the endplate 105 within the vertebral body 159, which can cause back pain. High lactic acid 162 concentration within the disc 100 can permeate through the porous endplate 105 to irritate and burn the nerves at the endplate 105. The lactic acid inhibitor 163 can be delivered through intra-vertebral body injection to alleviate back pain, as shown in FIG. 13. The needle 276B for injecting lactic acid inhibitor 163 can be elastically curved, and can be resiliently straightened within a straight needle. The straight needle punctures through the pedicle, and the curved needle 276B is then deployed from the straight needle toward the endplate 105 to inject lactic inhibitor 163 within the vertebral body 159. Lactic inhibitor 163 can also be delivered by intravenous injection or oral ingestion to alleviate back pain, caused by burning of lactic acid 162 within the vertebral body 159.

Figure 10:
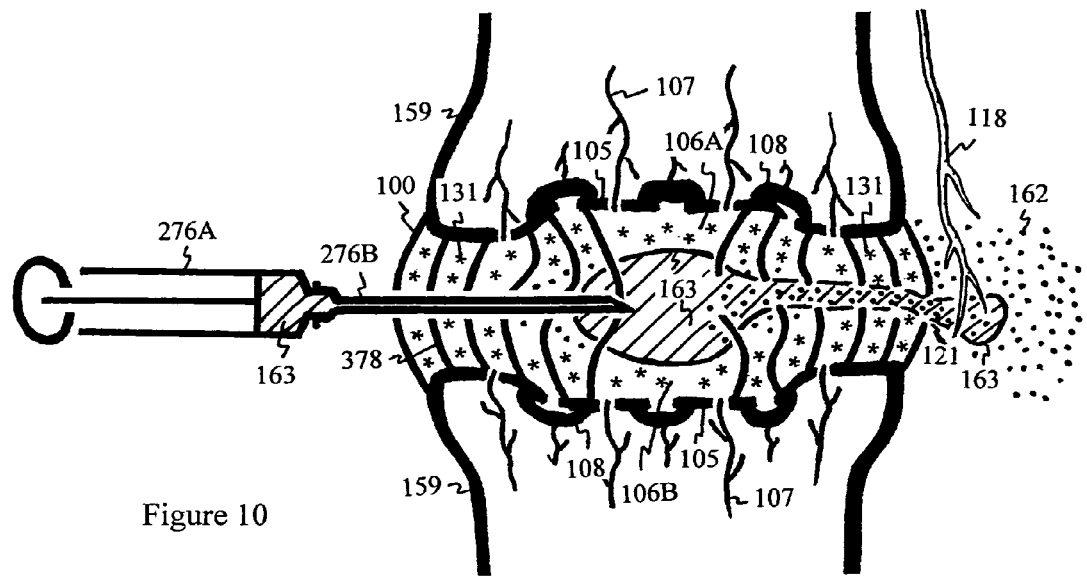
FIG. 10 shows a longitudinal view of intra-discal injection of lactic acid inhibitor 163 to inhibit production of lactic acid, especially within the mid-layer of the avascular disc 100.
Figure 11:
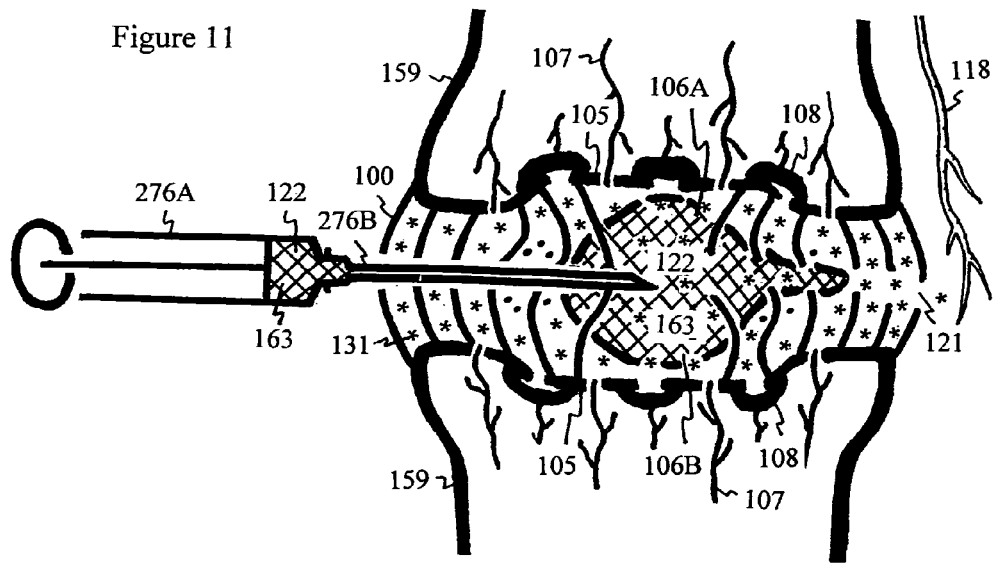
FIG. 11 shows combination intra-discal injection of alkaline/buffer chemical 122 and lactic acid inhibitor 163 to neutralize and inhibit production of the lactic acid within the avascular disc 100.

The lactic inhibitor 163 stops or reduces production of lactic acid 162 within the anaerobic and avascular disc 100. However, the lactic acid 162 within the disc can be flushed out during intra-discal injection of lactic inhibitor 163, thus causing excruciating pain to the patient, as shown in FIG. 10. For patient comfort, antacid, alkaline or buffering agent 122 can also be loaded with the lactic inhibitor 163 into the syringe 276A, and slowly injected into the painful disc 100 through the spinal needle 276B, as shown in FIG. 11. Before being flushed out the disc 100, the antacid, alkaline or buffer agent 122 instantaneously neutralizes the lactic acid 162 into pH neutral lactate, to avoid burning the surrounding nerves 118. The antacid, alkaline or buffering agent 122 and lactic inhibitor 163 can be intra-discal sequentially injected to neutralize the lactic acid 162, and then inhibit the production of the lactic acid 162.

Figure 12:
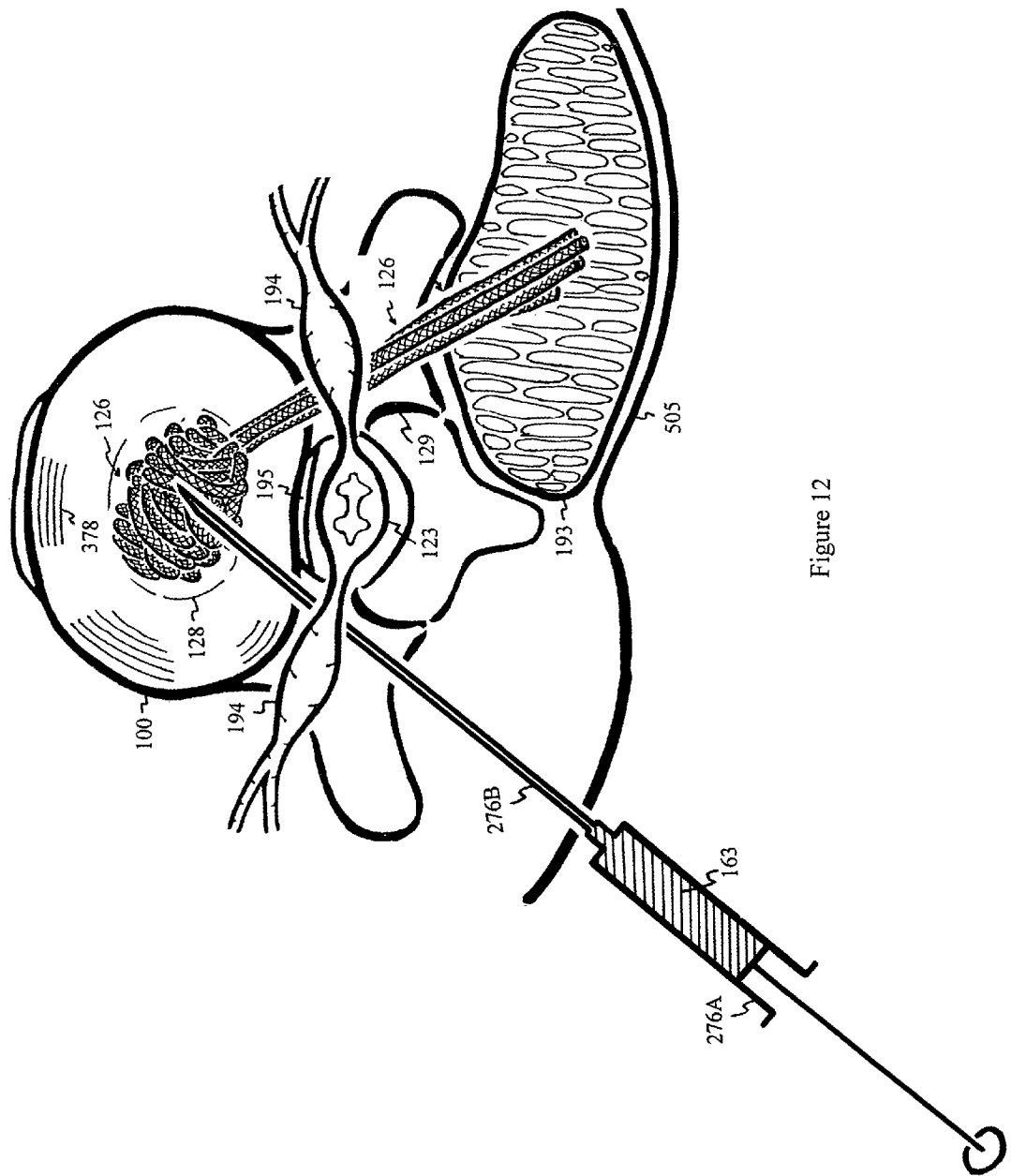
FIG. 12 shows intra-discal injection of lactic acid inhibitor 163 into a disc-shunted disc 100 to preserve pyruvate for aerobic metabolism into carbon dioxide and adenosine triphosphate (ATP).

Disc shunt 126 is a wick or conduit, capable of drawing blood plasma containing nutrients, oxygen and pH buffering solute 131 from muscle 193 and/or superior 106A and/or inferior 106B diffusion zones within the disc 100 into the mid-layer of the disc 100, as shown in FIG. 12. Sodium bicarbonate is a pH buffering solute 193 in blood plasma capable of neutralizing lactic acid 162 within the disc 100. Intra-discal injection of the lactic acid inhibitor 163 reduces or prevents conversion of pyruvate into lactic acid 162 within the disc 100. In the presence of oxygen through the disc shunt 126, pyruvate can be metabolized into carbon dioxide, generating many more adenosine triphosphate (ATP) to energize disc regeneration by building new disc matrix.

The disc shunt 126 can also be coated with lactic inhibitor 163 before implanting into the disc 100. In addition, the lactic inhibitor 163 can be injected near the disc shunt 126 within the muscle 193, so that the disc shunt 126 can draw the lactic inhibitor 163 from bodily circulation into the disc 100.

The rate of sulfate incorporation for biosynthesizing glycosaminoglycans is pH sensitive. The maximum rate of sulfate incorporation is with pH 7.2-6.9. The rate of sulfate incorporation drops about 32-40% in acidic pH within the disc [Ohshima H, Urban J P: The effect of lactate and pH on proteoglycan and protein synthesis rates in the intervertebral disc. Spine, September:17(9), 1079-82, 1992]. Hence, pH normalization with lactic inhibitor 163 will likely increase production of the water-retaining glycosaminoglycans and swelling pressure of the disc 100.

It is to be understood that the present invention is by no means limited to the particular chemicals or constructions disclosed herein and/or shown in the specification and drawings, but also includes any other chemical, analogues, modification, changes or equivalents within the scope of the claims. Any one or more of the chemicals or features described may be added to or combined with any of the other chemicals or embodiments to create alternative combinations of chemicals and embodiments.

It should be clear to one skilled in the art that the current chemicals, embodiments, materials, constructions, methods, tissues or injection sites are not the only uses for which the invention may be used. Different chemicals, analogues, materials, constructions, methods or device designs for introducing lactic inhibitor 163 can be substituted and used. Nothing in the preceding description should be taken to limit the scope of the present invention. The full scope of the invention is to be determined by the appended claims.

REFERENCE

1. Deyo R A, Weinstein J N: Low back pain, N Eng J Med, 344(5) February, 363-370, 2001.
2. Boswell M V, et. al.: Interventional Techniques: Evidence-based practice guidelines in the management of chronic spinal pain, Pain Physician, 10:7-111, ISSN 1533-3159, 2007.
4. Urban J P, Smith S, Fairbank J C T: Nutrition of the Intervertebral Disc, Spine, 29 (23), 2700-2709, 2004.
5. Benneker L M, Heini P F, Alini M, Anderson S E, Ito K: Vertebral endplate marrow contact channel occlusions & intervertebral disc degeneration, Spine V30, 167-173, 2005.
6. Holm S, Maroudas A, Urban J P, Selstam G, Nachemson A: Nutrition of the intervertebral disc: solute transport and metabolism, Connect Tissue Res., 8(2): 101-119, 1981.
7. Stairmand J W, Holm S, Urban J P G: Factor influencing oxygen concentration gradients in disc, Spine, Vol. 16, 4, 444-449, 1991
8. Maroudas A, Stockwell R A, Nachemson A, Urban J: Factors involved in the nutrition of the human lumbar intervertebral disc: Cellularity and diffusion of glucose in vitro, J. Anat., 120, 113-130, 1975.
3. Diamant B, Karlsson J, Nachemson A: Correlation between lactate levels and pH of patients with lumbar rizopathies, Experientia, 24, 1195-6, 1968.
4. Nachemson A: Intradiscal measurements of pH in patients with lumbar rhizopathies. Acta Orthop Scand, 40, 23-43, 1969.
5. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008.
6. Stockwell R A, Nachemson A, Urban J: Factors involved in the nutrition of human lumbar intervertebral disc: Cellularity and diffusion of glucose in vitro. J Anat, 120, 113, 1975.
7. Stairmand J W, Holm S, Urban J P G: Factors influencing oxygen concentration gradients in the intervertebral disc. Spine, 16(4), 444-9, 1991.
8. Kofoed H, Levander B: Respiratory gas pressure in the spine, measurements in goats. Acta Orthopaedic Scand, 58, 415-18, 1987.
9. Diamant B, Karlsson J, Nachemson A: Correlation between lactate levels and pH of patients with lumbar rizopathies, Experientia, 24, 1195-6, 1968.
10. Nachemson A: Intradiscal measurements of pH in patients with lumbar rhizopathies. Acta Orthop Scand, 40, 23-43, 1969.
11. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008.

12. Stockwell R A, Nachemson A, Urban J: Factors involved in the nutrition of human lumbar intervertebral disc: Cellularity and diffusion of glucose in vitro. J Anat, 120, 113, 1975.
13. Stairmand J W, Holm S, Urban J P G: Factors influencing oxygen concentration gradients in the intervertebral disc. Spine, 16(4), 444-9, 1991.
14. Kofoed H, Levander B: Respiratory gas pressure in the spine, measurements in goats. Acta Orthopaedic Scand, 58, 415-18, 1987.
15. Urban J P G, Holm S, Maroudas A, Nachemson A: Nutrition of the intervertebral disc. Clinical Orthopaedic and Related Research, 129 November-December, 101-14, 1977.
16. Holm S. Selstam G, Nachemson A: Carbohydrate metabolism and concentration profiles of solutes in the canine lumbar intervertebral disc. Acta Physiol Scand, 115, 147-56, 1982.
17. Bernick S, Cailliet R: Vertebral endplate changes with aging of human vertebrae. Spine, 7(2), 97-102, 1982.
18. Feinberg J, Boachie Adjei O, Bullough P G, Boskey A: The Distribution of calcified deposits in intervertebral discs of the lumbosacral spine. Clinical Orthopaedic and Related Research, 254 (May), 303-10, 1990.
19. Bernick S, Cailliet R, Levy B: The maturation and aging of the vertebrae of marmosets. Spine, 5(6, November/December), 519-24, 1980.
20. Aoki J, Yamamoto I, Kitamura N, Sone T, Itoh H, Torizuka K, Takasu K: Endplate of the discovertebral joint: Degenerative change in the elderly adult. Radiology, August, 411-4, 1987.
91. O'Connor F G, Marlowe S S: Low back pain in military basic trainees. A pilot study. Spine, August; 18(10):1351-4, 1993.
92. Iwahashi M, Matsuzaki H, Tokuhashi Y, Wakabayashi K, Uematsu Y: Mechanism of intervertebral disc degeneration caused by nicotine in rabbits to explicate intervertebral disc disorders caused by smoking. Spine, July 1; 27(13):1396-401, 2002.
93. Fogelholm R R, Alho A V: Smoking and intervertebral disc degeneration. Med Hypotheses, April; 56(4):537-9, 2001.
94. Hanley E N Jr, Shapiro D E: The development of low-back pain after excision of a lumbar disc. J Bone Joint Surg Am. June; 71(5):719-21, 1989.
95. Hambly M F, Mooney V: Effect of smoking and pulsed electromagnetic fields on intradiscal pH in rabbits. Spine, June; 17(6 Suppl):S83-5, 1992.
96. Uematsu Y, Matuzaki H, Iwahashi M: Effects of nicotine on the intervertebral disc: an experimental study in rabbits, J Orthop Sci. 6(2):177-82. 2001.
97. Holm S, Nachemson A: Nutrition of the intervertebral disc: acute effects of cigarette smoking. An experimental animal study. Ups J Med. Sci. 93(1):91-9, 1988.
98. Kurunlahti M, Tervonen O, Vanharanta H, Ilkko E, Suramo I: Association of atherosclerosis with low back pain and the degree of disc degeneration. Spine, October 15; 24(20):2080-4, 1999.
99. Tatsuro K, Zerwekh J, Usui Y, Edwards M L, Flicker P L, Mooney V: Biochemical changes associated with the symptomatic human intervertebral disk, Clinical Orthopaedics and Related Research, Number 293, 372-377, 1993.
108. Gregory Livshits, Sergey Ermakov, Maria Popham, 1 Alex J MacGregor, Philip N Sambrook Timothy D Spector, Frances M K Williams: Evidence that bone mineral density plays a role in degenerative disc disease: the UK Twin Spine Study, Ann Rheum Dis; 69:2102-2106, 2010.
109. Videman T, Leppavuori J, Kaprio J, Battle M C, Gibbons L E, Peltonen L, Koskenvuo M: Intragenic polymorphisms of the Vitamin D receptor gene associated with intervertebral disc degeneration. Spine, 23(23), 2477-85, 1998.
110. S. Rajasekaran, K. Venkatadass, J. Naresh Babu, K. Ganesh, Ajoy P. Shetty: Pharmacological enhancement of disc diffusion and differentiation of healthy, ageing and degenerated discs. Results from in-vivo serial post-contrast MRI studies in 365 human lumbar discs, Eur Spine J 17:626-643 (2008).
116. Stefanakis M, Al-Abbasi M, Harding I, Pollintine P, Dolan P, Tarlton J, Adams M A: Annulus fissures are mechanically and chemically conducive to the ingrowth of nerves and blood vessels, Spine (phila Pa 1976), October 15; 37(22):1883-91, 2012.
117. Freemont A J, Peacock T E, Goupille P, Hoyland J A, O'Brien J, Jayson M I: Nerve ingrowth into diseased intervertebral disc in chronic back pain, Lancet, July 19; 350 (9072):178-81, 1997.
118. Melrose J, Roberts S, Smith S, Menage J, Ghosh P: Increased nerve and blood vessel ingrowth associated with proteoglycan depletion in an ovine anular lesion model of experimental disc degeneration, Spine (Phila Pa. 1976), June 15; 27(12): 1278-1285, 2002
119. Kallewaar J W, Terheggen M A, Groen G J, Sluijter M E, Derby R, Kapural L, Mekhail N: 15. Discogenic low back pain, Pain Pract. November-December; 10(6):560-579, 2010.
120. Podichetty V K: The aging spine: the role of inflammatory mediators in intervertebral disc degeneration, Cell Mol Biol (Noisy-le-grand), May 30; 53(5):4-18, 2007.
121. Moon H J, Kim J H, Lee H S, Chotai S, Kang J D, Suh J K, Park Y K: Annulus fibrosus cells interact with neuron-like cells to modulate production of growth factors and cytokines in symptomatic disc degeneration, Spine (Phila Pa. 1976), Jan 1; 37(1):2-9, 2012.
122. Tolofari S K, Richardson S M, Freemont A J, Hoyland J A: Expression of semaphorin 3A and its receptors in the human intervertebral disc: potential role in regulating neural ingrowth in the degenerate intervertebral disc, Arthritis Res Ther. 12(1):R1, 2010.
123. Brisby H: Pathology and possible mechanisms of nervous system response to disc degeneration, J. Bone Joint Surg Am., April; 88 Suppl 2:68-71, 2006.
124. Aoki Y, Ohtori S, Ino H, Douya H, Ozawa T, Saito T, Moriya H, Takahashi K: Disc Inflammation potentially promotes axonal regeneration of dorsal root ganglion Neurons innervating lumbar intervertebral disc in rats, Spine (Phila Pa. 1976), December 1; 29(23):2621-6, 2004.
125. Carragee E J, Cheng I: Minimum acceptable outcomes after spinal fusion, The Spine Journal 10, 313-320, 2010.
126. Ostelo R W J G, Deyo R A, Stratford P, Waddell G, Croft P, Von Korff M, Bouter L M, de Vet H C: Interpreting change scores for pain and functional status in low back pain, Spine Volume 33, Number 1, 90-94, 2008.
127. Copay A G, Glassman S D, Subach B R, Berven S, Schuler T C, Carreon L Y: Minimum clinical important difference in lumbar spine surgery patients: a choice of methods using the Oswestry Disability Index, Medical Outcomes Study questionnaire Short Form 36, and Pain Scales, The Spine Journal 8, 968-974, 2008.

What is claimed is:

1. A method for reducing lactic acid within an intervertebral disc, the method comprising the steps of:
   (a) inserting a needle into an intervertebral disc,
   (b) filling a lactic acid inhibitor in a syringe,
   (c) connecting said syringe to said needle,
   (d) injecting said lactic acid inhibitor in said syringe through said needle into the intervertebral disc to inhibit production of lactic acid, thereby alleviating back pain from lactic acid burn,
   (e) removing said needle from the intervertebral disc.

2. The method for reducing lactic acid within an intervertebral disc of claim 1, wherein in step (d) said lactic acid inhibitor is injected by actuating a plunger in said syringe.

3. The method for reducing lactic acid within an intervertebral disc of claim 1, wherein in step (a) a beveled tip of said needle is used to puncture the intervertebral disc.

4. The method for reducing lactic acid within an intervertebral disc of claim 1, wherein in step (b) said lactic acid inhibitor is a lactate dehydrogenase inhibitor.

5. The method for reducing lactic acid within an intervertebral disc of claim 1, wherein said lactic acid inhibitor is chosen from the group of lactic acid inhibitors consisting of: fluoropyruvic acid, fluoropyruvate, levulinic acid, levulinate, oxamic acid, N-substituted oxamic acids, oxamate, oxalic acid, oxalate, beta-bromopropionate, beta-chloropropionate, malonate, sodium formaldehyde bisufite, chloroacetic acid, alpha-chloropropionate, alpha-bromopropionate, beta-iodopropionate, acrylate, acetoin, malic acid, glycolate, diglycolate, acetamide, acetaldehyde, acetylmercaptoacetic acid, alpha ketobutyrate, thioglycolic acid, nicotinic acid, alpha-ketoglutarate, butanedione, hydroxypyruvic, chloropyruvic, bromopyruvic, 2,3-dihydroxy-6-methyl-4-(1-methylethyl)-1-naphthoic acid, diethyl pyrocarbonate, hexyl N,N-diethyloxamate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 (Cibacron Blue 3G-A) urea, methylurea and hydantoic acid, glyoxylate, hydroxybutyrate, 4-hydroxyquinoline-2-3 carboxylic acids, sodium bisulfite, dieldrin, L-(+) beta monofluorolactic acid, fluoro-lactic acid, tartronic acid, mesotartarate, sesquiterpene 8-deoxyhemigossylic acid (2,3-dihydroxy-6-methyl-4-(1-methylethyl)-1-naphthoic acid), and analogues of these chemicals.

6. The method for reducing lactic acid within an intervertebral disc of claim 1, wherein said lactic acid inhibitor in step (b) is a NADH dehydrogenase inhibitor.

7. The method for reducing lactic acid within an intervertebral disc of claim 6, wherein said NADH dehydrogenase inhibitor is chosen from the group of NADH dehydrogenase inhibitors consisting of: gossypol, polyphenol, dihydroxynaphthoic acids, adenosine diphosphate ribose, rotenone, rotenoid, phenoxan, aureothin, benzimidazole, acetogenin, nitrosothiols, peroxynitrite, carvedilol, arylazido-beta-alanyl NAD+, piericidin A, annonin VI, phenalamid $A_2$, aurachins A and B, thiangazole, fenpyroximate, adriamycin, 4-hydroxy-2-nonenal, pyridine derivatives, 2-heptyl-4-hydroxyquinoline N-oxide, dicumarol, o-phenanthroline and 2,2'-dipyridyl.

8. A method of reducing lactic acid within an intervertebral disc in claim 1, wherein in step (b) further comprises filling an antacid in said syringe, and wherein in step (d) further comprises injecting said antacid into the intervertebral disc to neutralize lactic acid, thereby instantly alleviating back pain from lactic acid burn.

9. A method for reducing lactic acid within an intervertebral disc of claim 1, wherein said needle in step (a) is a curved needle.

10. A method for reducing lactic acid within an intervertebral disc of claim 9, wherein said curved needle is resiliently straightened within a straight needle.

11. A method for reducing lactic acid within a vertebral body, the method comprising the steps of:
   (a) inserting a needle into a vertebral body,
   (b) filling a lactic acid inhibitor in a syringe,
   (c) connecting said syringe to said needle,
   (d) injecting said lactic acid inhibitor in said syringe through said needle into the vertebral body to inhibit production of lactic acid, thereby alleviating back pain from lactic acid burn,
   (e) removing said needle from the vertebral body.

12. A method for reducing lactic acid within a vertebral body of claim 11, wherein in step (b) further comprises filling an antacid in said syringe, and wherein in step (d) further comprises injecting said antacid into the vertebral body to neutralize lactic acid, thereby instantly alleviating back pain from lactic acid burn.

13. A method for reducing lactic acid within a vertebral body of claim 11, wherein said lactic acid inhibitor in step (d) is injected by actuating a plunger in said syringe.

14. The method for reducing lactic acid within a vertebral body of claim 11, wherein said lactic acid inhibitor is chosen from the group of lactic acid inhibitors consisting of: fluoropyruvic acid, fluoropyruvate, levulinic acid, levulinate, oxamic acid, N-substituted oxamic acids, oxamate, oxalic acid, oxalate, beta-bromopropionate, beta-chloropropionate, malonate, sodium formaldehyde bisufite, chloroacetic acid, alpha-chloropropionate, alpha-bromopropionate, beta-iodopropionate, acrylate, acetoin, malic acid, glycolate, diglycolate, acetamide, acetaldehyde, acetylmercaptoacetic acid, alpha ketobutyrate, thioglycolic acid, nicotinic acid, alpha-ketoglutarate, butanedione, hydroxypyruvic, chloropyruvic, bromopyruvic, 2,3-dihydroxy-6-methyl-4-(1-methylethyl)-1-naphthoic acid, diethyl pyrocarbonate, hexyl N,N-diethyloxamate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 (Cibacron Blue 3G-A) urea, methylurea and hydantoic acid, glyoxylate, hydroxybutyrate, 4-hydroxyquinoline-2-3 carboxylic acids, sodium bisulfite, dieldrin, L-(+) beta monofluorolactic acid, fluoro-lactic acid, tartronic acid, mesotartarate, sesquiterpene 8-deoxyhemigossylic acid (2,3-dihydroxy-6-methyl-4-(1-methylethyl)-1-naphthoic acid), and analogues of these chemicals.

15. The method for reducing lactic acid within a vertebral body of claim 11, wherein said lactic acid inhibitor in step (b) is a NADH dehydrogenase inhibitor.

16. The method for reducing lactic acid within a vertebral body of claim 15, wherein said NADH dehydrogenase inhibitor is chosen from the group of NADH dehydrogenase inhibitors consisting of: gossypol, polyphenol, dihydroxynaphthoic acids, adenosine diphosphate ribose, rotenone, rotenoid, phenoxan, aureothin, benzimidazole, acetogenin, nitrosothiols, peroxynitrite, carvedilol, arylazido-beta-alanyl NAD+, piericidin A, annonin VI, phenalamid $A_2$, aurachins A and B, thiangazole, fenpyroximate, adriamycin, 4-hydroxy- 2-nonenal, pyridine derivatives, 2-heptyl-4-hydroxyquinoline N-oxide, dicumarol, o-phenanthroline and 2,2'-dipyridyl.

17. A method for reducing lactic acid within a vertebral body of claim 11, wherein said needle in step (a) in is a curved needle.

18. A method for reducing lactic acid within a vertebral body of claim 17, wherein said curved needle is resiliently straightened within a straight needle.

19. A method for reducing lactic acid within an intervertebral disc, the method comprising the steps of:
 (a) coating a disc shunt with a lactic acid inhibitor,
 (b) implanting said disc shunt into the intervertebral disc to inhibit production of lactic acid, thereby alleviating back pain from lactic acid burn.

20. The method for reducing lactic acid within an intervertebral disc of claim 19, wherein said lactic acid inhibitor is chosen from the group of lactic acid inhibitors consisting of: fluoropyruvic acid, fluoropyruvate, levulinic acid, levulinate, oxamic acid, N-substituted oxamic acids, oxamate, oxalic acid, oxalate, beta-bromopropionate, beta-chloropropionate, malonate, sodium formaldehyde bisufite, chloroacetic acid, alpha-chloropropionate, alpha-bromopropionate, beta-iodopropionate, acrylate, acetoin, malic acid, glycolate, diglycolate, acetamide, acetaldehyde, acetylmercaptoacetic acid, alpha ketobutyrate, thioglycolic acid, nicotinic acid, alpha-ketoglutarate, butanedione, hydroxypyruvic, chloropyruvic, bromopyruvic, 2,3-dihydroxy-6-methyl-4-(1-methylethyl)-1-naphthoic acid, diethyl pyrocarbonate, hexyl N,N-diethyloxamate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 (Cibacron Blue 3G-A) urea, methylurea and hydantoic acid, glyoxylate, hydroxybutyrate, 4-hydroxyquinoline-2-3 carboxylic acids, sodium bisulfite, dieldrin, L-(+) beta monofluorolactic acid, fluoro-lactic acid, tartronic acid, mesotartarate, sesquiterpene 8-deoxyhemigossylic acid (2,3-dihydroxy-6-methyl-4-(1-methylethyl)-1-naphthoic acid), and analogues of these chemicals.

* * * * *